United States Patent [19]

McCombs et al.

[11] 4,441,506
[45] Apr. 10, 1984

[54] RESPIRATORY EXERCISER

[75] Inventors: Norman R. McCombs, 109 Millwood La., Tonawanda, N.Y. 14150; Grace N. McCombs, Tonawanda, N.Y.

[73] Assignee: Norman McCombs, Tonawanda, N.Y.

[21] Appl. No.: 264,969

[22] Filed: May 18, 1981

[51] Int. Cl.³ .................... A61B 5/08; A63B 23/00
[52] U.S. Cl. ................................. 128/728; 272/99
[58] Field of Search ............ 128/725, 727, 728, 730, 128/205.16; 285/24, 260, 200, 192, 7; 29/235, 157; 272/99; 73/168, 149; 92/34, 26, 40, 43, 45

[56] References Cited

U.S. PATENT DOCUMENTS

| 2,807,079 | 9/1957 | Josephson | 29/235 |
| 3,481,310 | 12/1969 | Alburger | 285/192 |
| 3,650,551 | 3/1972 | Akers | 285/200 |
| 3,993,050 | 11/1976 | Robinson et al. | 128/728 |
| 4,324,260 | 4/1982 | Puderbaugh | 128/728 |
| 4,345,605 | 8/1982 | Gereg | 128/728 |
| 4,349,015 | 9/1982 | Alferness | 128/205.16 |
| 4,363,328 | 12/1982 | Poirier et al. | 128/728 |

FOREIGN PATENT DOCUMENTS

| 27154 | 4/1981 | European Pat. Off. | 128/728 |
| 890125 | 9/1942 | France | 128/728 |
| 2062470 | 5/1981 | United Kingdom | 128/728 |

Primary Examiner—Henry J. Recla
Assistant Examiner—Karin M. Reichle
Attorney, Agent, or Firm—Browdy & Neimark

[57] ABSTRACT

A respiratory exerciser having the features of being fabricated from cardboard and plastic stamped parts which are glued together and which fold up into a compact box for ease of storage including stowage of the connecting hose and mouthpiece inside the box. Many different forms, variations and optional features are also provided.

52 Claims, 26 Drawing Figures

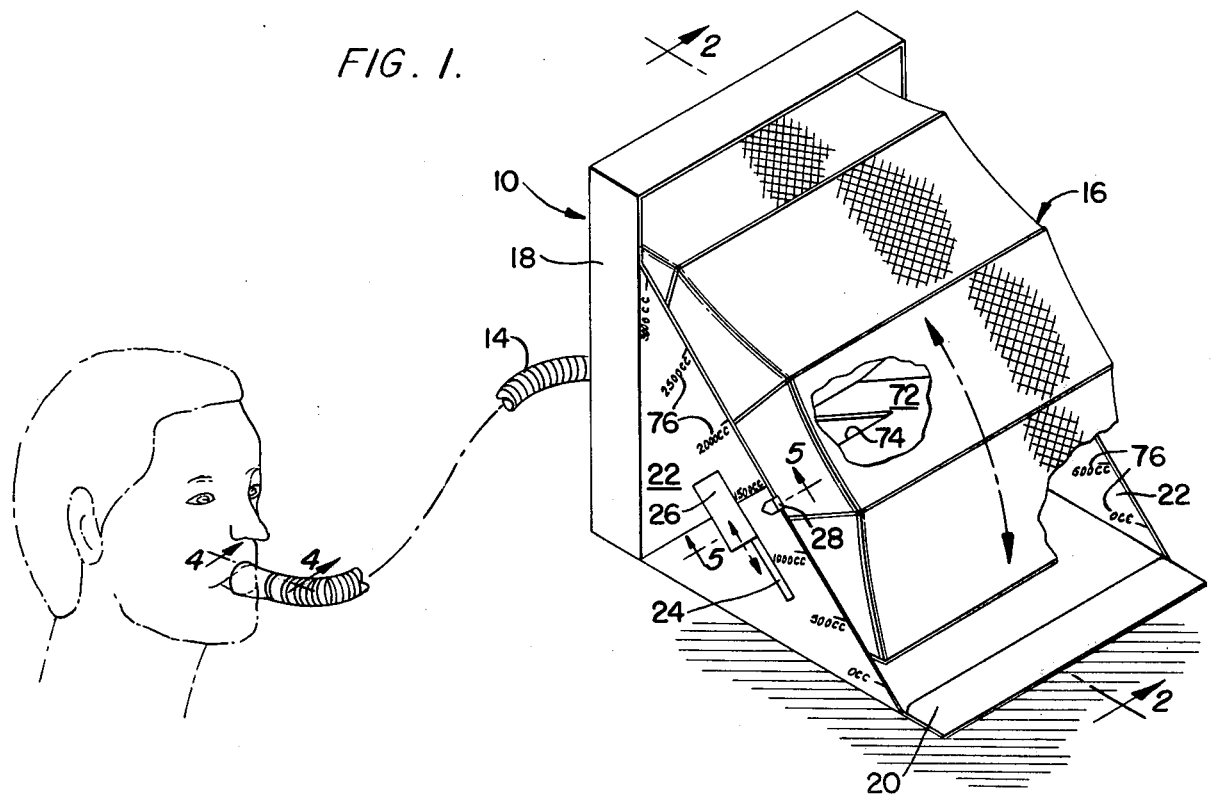
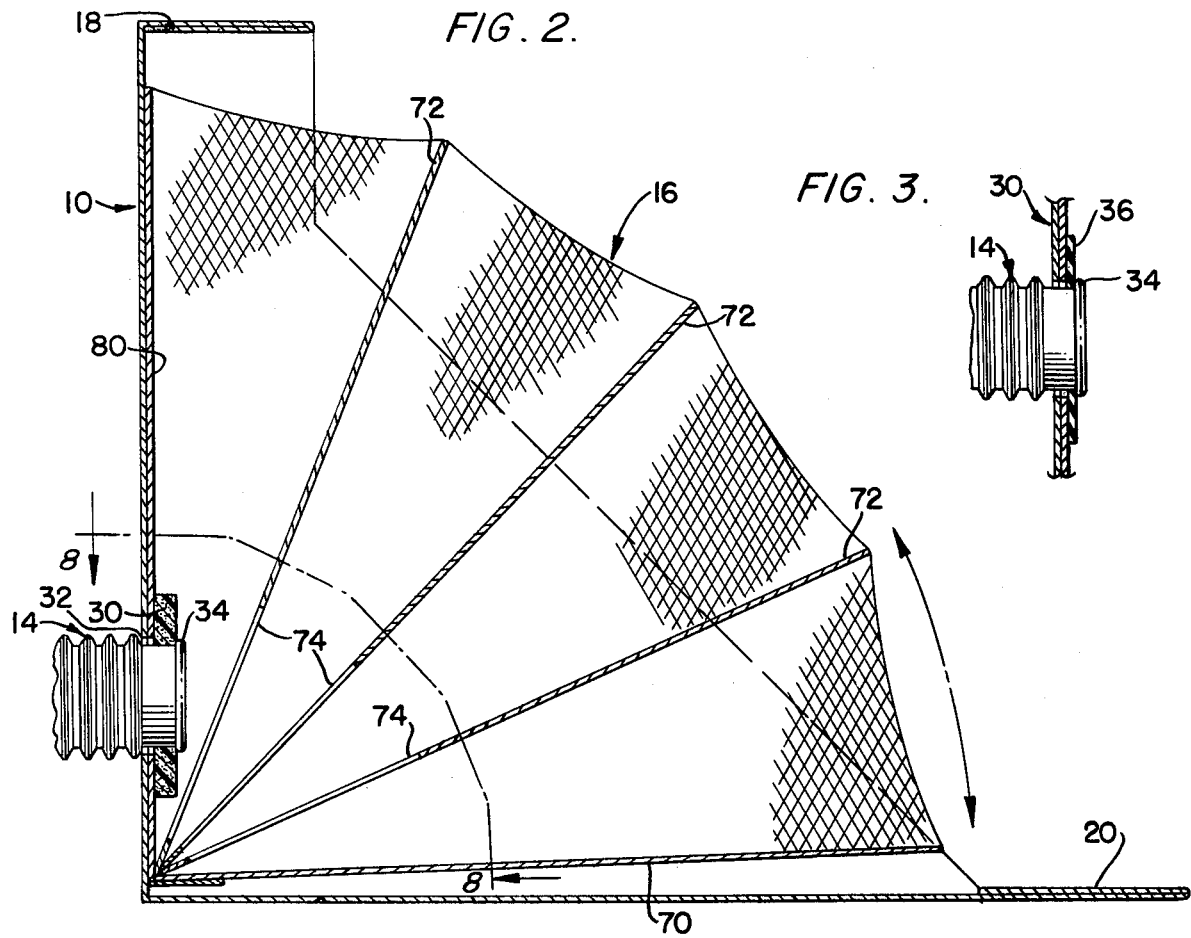

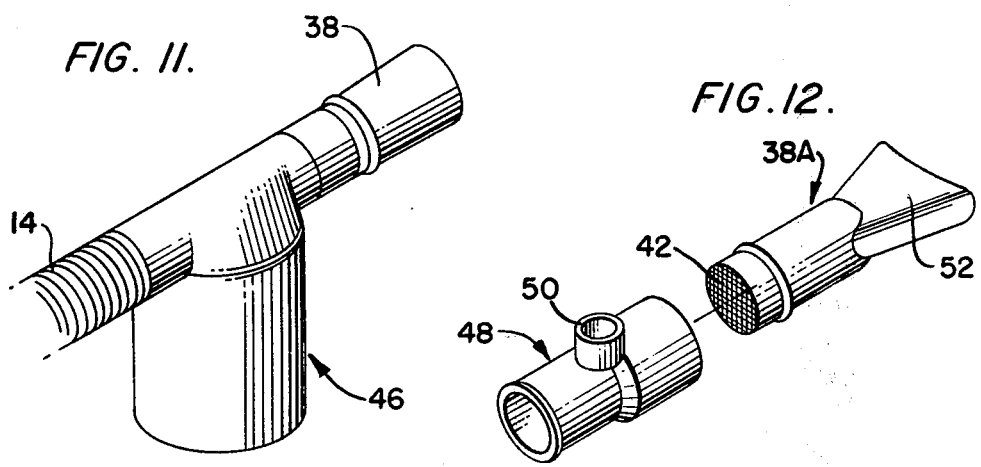
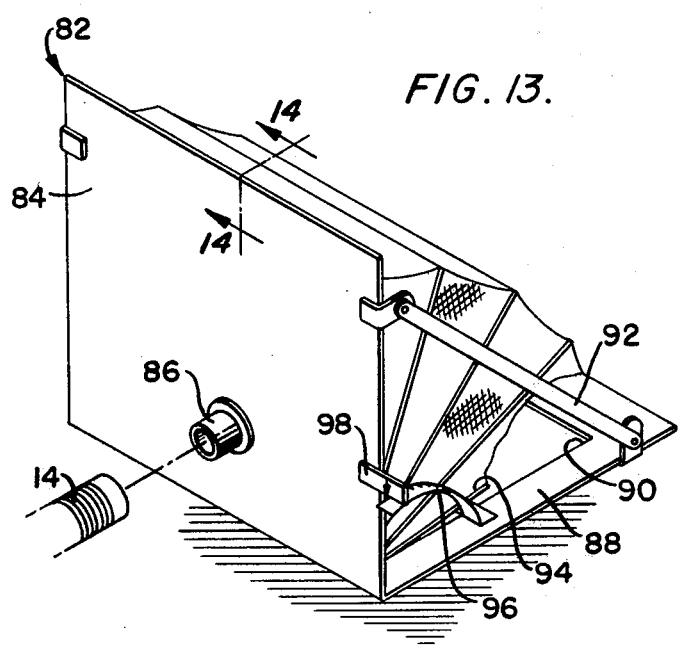
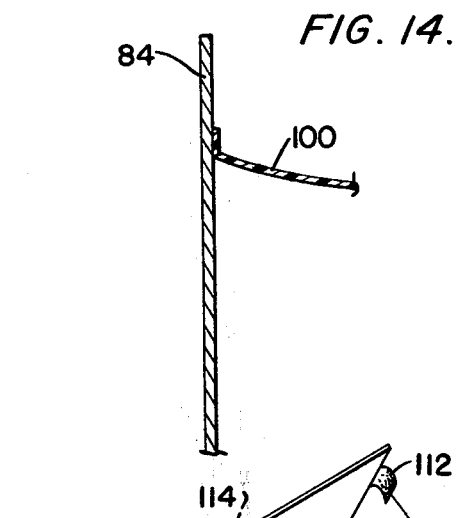
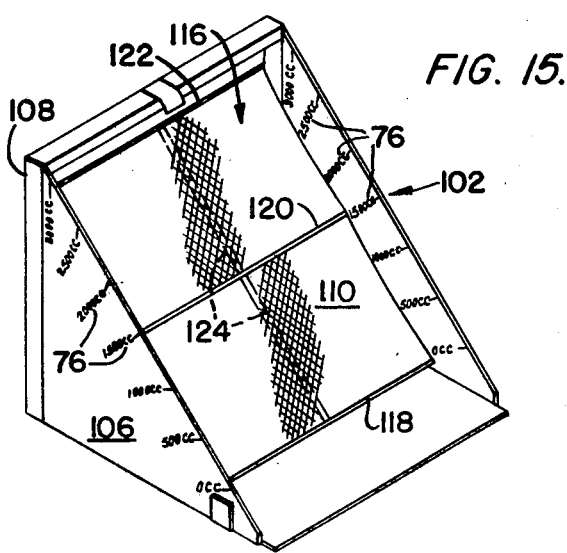
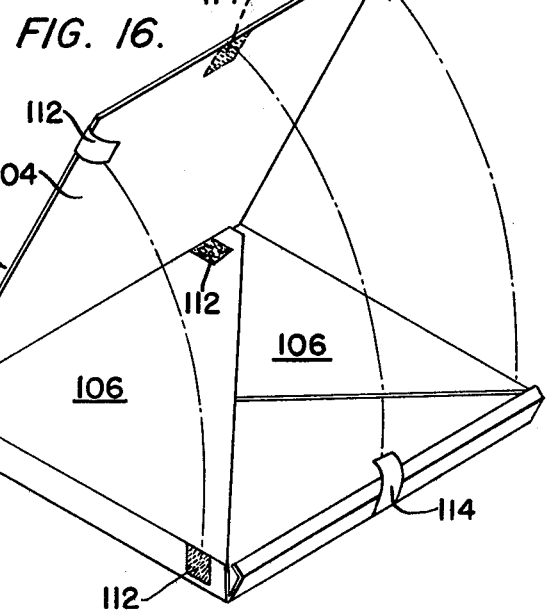

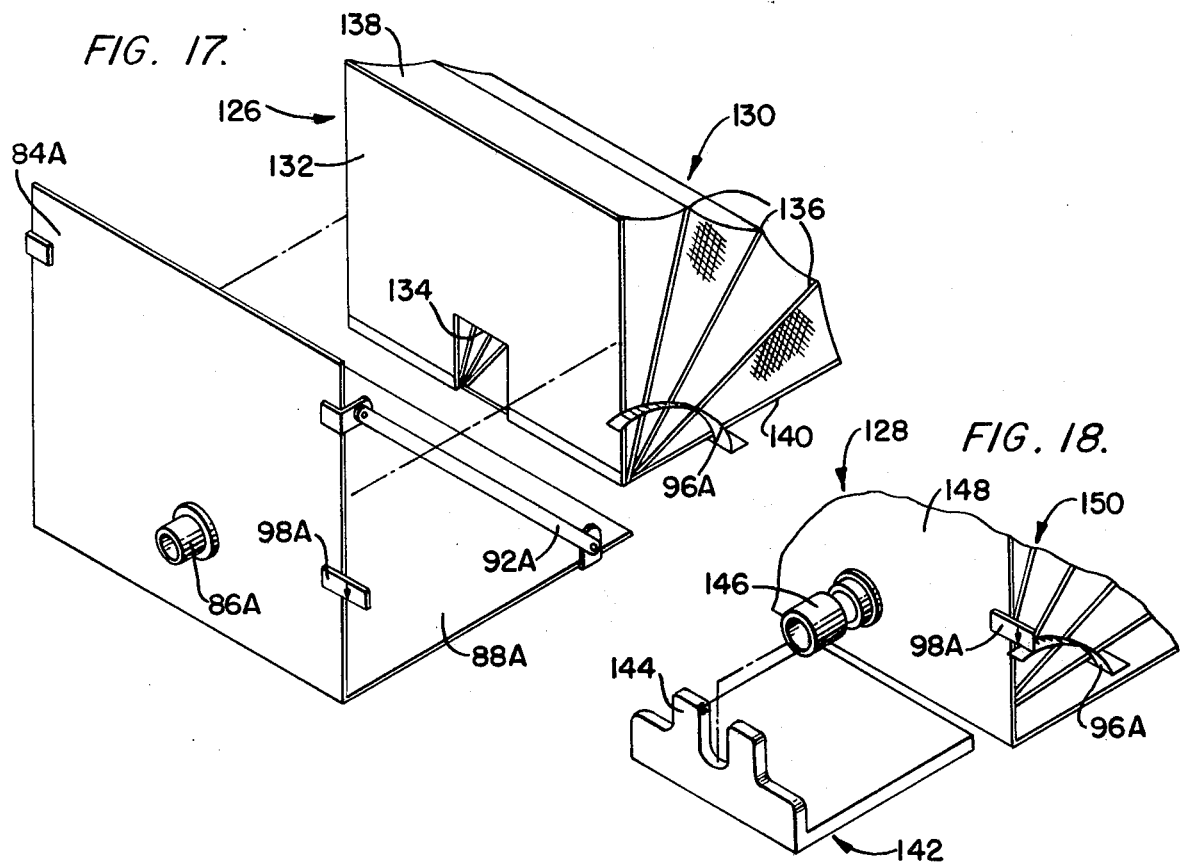
FIG. 17.
FIG. 18.
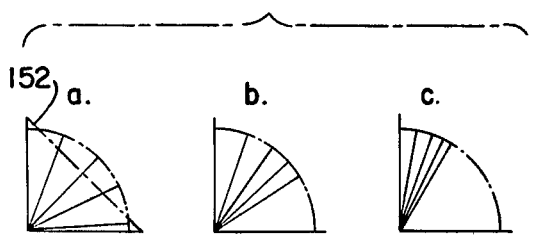
FIG. 19.
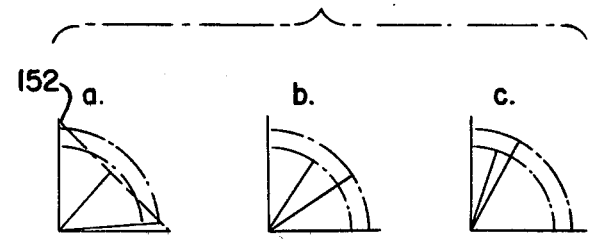
FIG. 20.
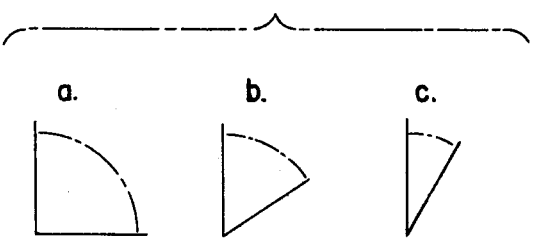
FIG. 21.
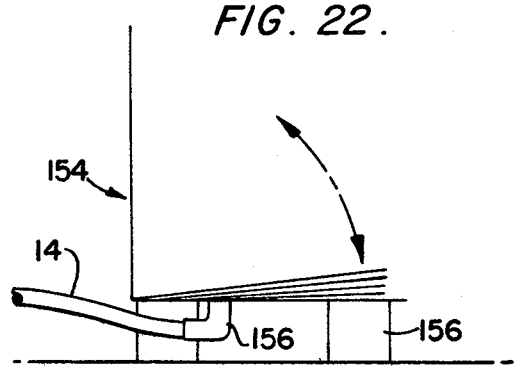
FIG. 22.

RESPIRATORY EXERCISER

This invention pertains to a respiratory exerciser for medical purposes.

The term "respiratory exerciser" as used in the specification and claims herein shall be understood to include spirometers and the like devices which are routine tools for measuring lung capacity on both inhaling and exhaling, as well as incentive breathing devices. "Incentive breathing devices" shall be understood to mean those which are used in conjunction with rehabilitating people who have undergone surgery, particularly abdominal injury, which makes it painful or difficult for such patients to breathe normally. Prolonged dis-use of the lungs, as is caused by shallow breathing in such situations, can cause various ailments including collapse of a lung or atelectasis in such patients. Thus, hospitals routinely provide this type of therapy or rehabilitation, that is incentive breathing, after such surgery, to be sure that the patient re-learns breathing normally to prevent this deterioration of lung capacity which would otherwise occur. The invention was developed primarily for this incentive breathing use, but it is also applicable to spirometers, and other respiratory and other air handling uses. Thus the term "respiratory device" and the like as used in the specification and claims herein shall be understood to include all such applications as well as the various embodiments of the invention disclosed.

It is anticipated that the invention can be used in areas other than the medical area since it lends itself to many and greatly different types and sizes without any changes in concept, and with only minor changes in manufacturing, due to its extremely simple manner of manufacture, as is explained in greater detail below.

Since the invention was developed primarily as an incentive breathing exerciser rather than any other kind of respiratory device, it is described primarily in that context, it being understood however that the scope of protection is not to be so limited.

An important advantage of the invention is that it is a single patient disposable device, as opposed to a permanent machine as has heretofore been common. This major change provides substantial advantages for both the patient and the hospitals and other users of the invention. Prior art machines were large and bulky and require a substantial capital investment, maintenance, moving from patient to patient, suffered from the possibility of there being insufficient machines for the patients requiring such therapy at any particular time, required sanitary arrangements, interchangeable mouthpieces, and the like, and suffered from various other problems overcome by providing a disposable device. The prior art includes other disposable devices, but they are characterized by being extremely complex, including valves, moving parts, springs, and the like, all of which are not present in the present invention.

The invention is compact and comprises a "book-like" hinged bellows device which is housed in a box. "Book-like" in this context means that the bellows action opens and closes in the manner of the leaves of a book. The box includes side gussets which cooperate with the bellows in operation. The box and bellows are constructed such that the hose and the mouthpiece are stored inside the box. Thereafter, the manufacturer can house the entire device, including the hose and all operative parts, i.e., the complete kit, in a bag or other sterile enclosure, and this can be stored by the hospital for extremely long periods of time until needed. Thus, the invention, folded, produces a very compact package. Storage space in hospitals is extremely limited, and the advantage of the invention compared to both reusable machines as well as other prior art disposable or semi-disposable devices, is greatly enhanced. That is, the invention is much smaller than either the prior devices or permanent machines, thus providing other advantages in that area.

Most such prior art disposable or semi-disposable devices have mechanical parts, holding fingers, pressure release valves, and the like, which make them tremendously more expensive to manufacture and sell, as well as more prone to breakdown and failure, compared to the simple, reliable structure of the present invention. Many of these prior art devices have a vertical or straight acting bellows, as opposed to the book-like bellows of the present invention. This change in structure is important in aiding the invention in achieving its improved compactness for storage and the like.

Another advantage of the invention is that it is manufactured from very inexpensive and simple materials. It comprises a fabricated assemblage of paper, cardboard and sheet plastic, all glued and taped together. This structure lowers the capital cost for tooling to almost zero, thus, producing a low manufacturing cost item for the manufacturer of the invention devices.

A patient using the invention device is given one for his own personal use. He may use it for several days or perhaps several weeks while undergoing therapy. When the patient is recovered, the device is discarded.

In operation, the invention device is total volume rather than rate or flow dependent. In the prior art, there are devices which are rate dependent as opposed to being dependent upon total volume. The total volume approach is more desirable since it relates directly to the goal, i.e., the measuring and the increasing of the patient's lung capacity. With flow or rate type devices a formula must be handled based on flow times time, to come to capacity, or total volume. These additional steps can also require an additional mechanism to result in a more complex device, and add a degree of uncertainty and a source of error. Volume devices are not per se new, but the invention in common with its class of volume devices is to be differentiated from flow type devices which have numerous disadvantages not in volume type devices.

Another feature common in the prior art is springs of various sorts which operate opposite the effort of the user. The present invention operates with gravity as opposed to any spring, and this is deemed a substantial step forward. A spring, in addition to adding to manufacturing cost and complexity, is also a variable factor. That is, springs cannot be manufactured identically, and thus one device would not have exactly the same characteristics as another device. This uncertainty and additional error factor is eliminated in the invention by the elimination of the spring. The invention depends upon gravity for its return after each breath by the user. In addition, the force of the spring need not be overcome by the user in the present invention, since there is no spring, and thus the invention can be used by persons with drastically impaired breathing ability.

Many of these prior art devices, both with and without springs, and both volume and flow type, include bellows of various sorts. These bellows are frequently made of plastic or rubber materials, and involve complex molding operations for their manufacture. The present invention includes fabricated bellows of extremely simple and inexpensive designs. The invention bellows comprises a plurality of vanes, consisting of flat pieces of cardboard or the like, which are hinged at one end in book-like fashion, and whose outer ends and sides are covered by a thin sheet of plastic material. The ends are folded into and secured at the hinge, as well as to all of the edges of each of the vanes, to thereby constitute a bellows which is easily manufactured from cut and stamped parts, with virtually no cost for tooling. This provides a substantial economic advantage over all of those prior art devices having molded bellows of any sort.

Another aspect of the invention as compared to the prior art, including those having book-type bellows, is that such prior art bellows often operate with a fixed horizontal plane or vane and a moving vertical plane. The present invention is the opposite, the vertical vane is fixed and the horizontal vane moves. This is the arrangement which permits gravity to return the device to its beginning operating position between breaths by the user. Since the present invention is used as an incentive breathing device on inspirational breaths, it is particularly advantageous to have the moving horizontal plane. Further, the parts are proportioned and sized so that gravity will return the moving horizontal plane at a rate of speed closely matching or exceeding the normal pace desired by the user to exercise with the invention device. However, the invention also provides means to adjust this speed, including changing of size of orifices, adding weights to increase the speed, and the like. As an incidental matter, a weight does not have the disadvantages of springs as set forth above in that it is static and easily controlled. That is, a given weight at a given position will always produce the same effect, without the manufacturing variations that one encounters in springs per se and variations in positioning the spring in the apparatus. Further, a spring increases in resistance as it is compressed, whereas a weight is a constant.

The invention may also include various devices that cooperate with the box-like construction of the invention to provide a changing "target" of inspirational ability for the patient as he uses the device and re-builds his strength.

Thus, there is provided a respiratory exerciser of the character described which is of extremely simple and inexpensive construction, which folds into a box for easy storage in hospital store rooms and the like, which includes a moving horizontal plane rather than a moving vertical plane, which provides a gravity rather than a spring assist for return, which folds up compactly including storage of the hose and mouthpiece inside this small box, which uses standard respiratory hose and a plurality of mouthpieces all of which include a screen to prevent inhalation of foreign matter by the patient, and which is yet highly durable and reliable in use. It also includes a simplified bellows made of glued together stamped out cardboard and plastic parts.

The invention provides very little resistance to a patient's breathing effort. This is a particularly important advantage over the prior art in general, and especially so in geriatric and very severe cases.

The above and other advantages of the invention will be pointed out or will become evident in the following detailed description and claims, and in the accompanying drawing also forming a part of the disclosure, in which:

FIG. 1 is a perspective view of the preferred form of the invention showing the assembled device with a user in phantom lines;

FIG. 2 is a vertical cross-section taken on line 2—2 of FIG. 1;

FIG. 3 is a partial elevational view of a variation of a detail shown in FIG. 2;

Figure 4:
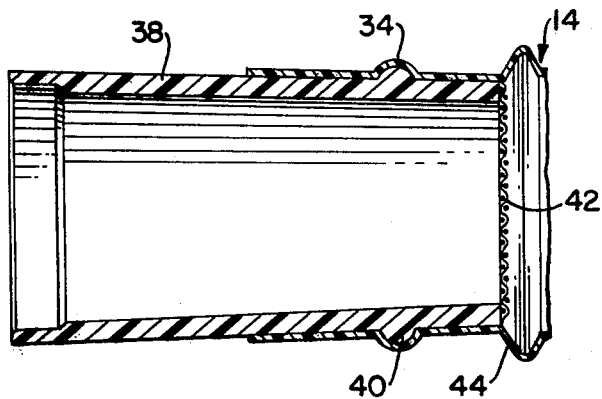
Figure 5:
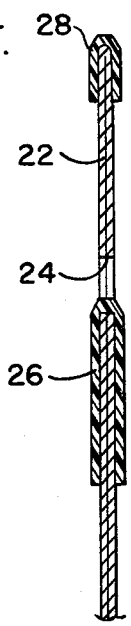
Figure 6:
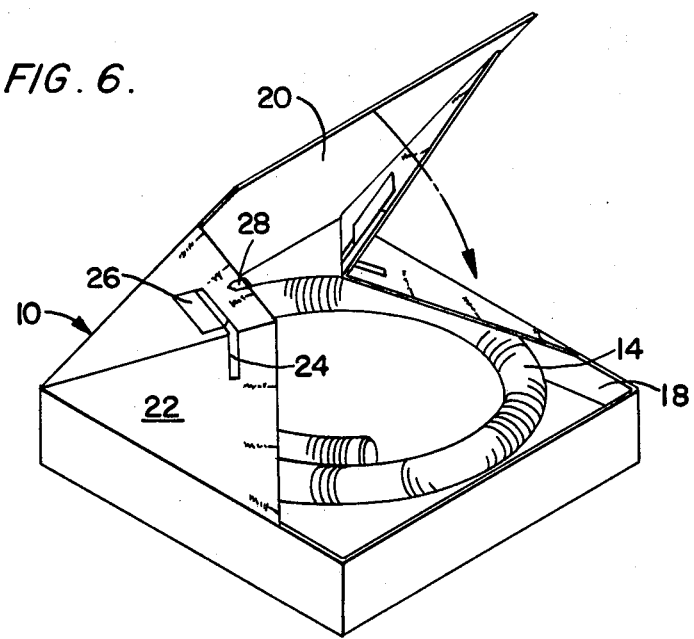
Figure 7:
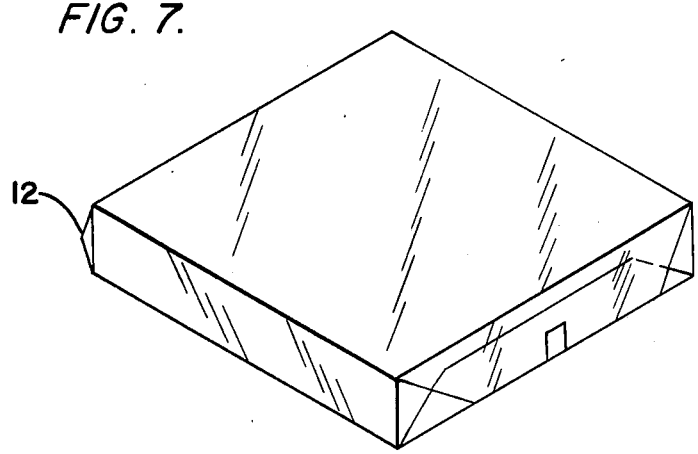
Figure 8:
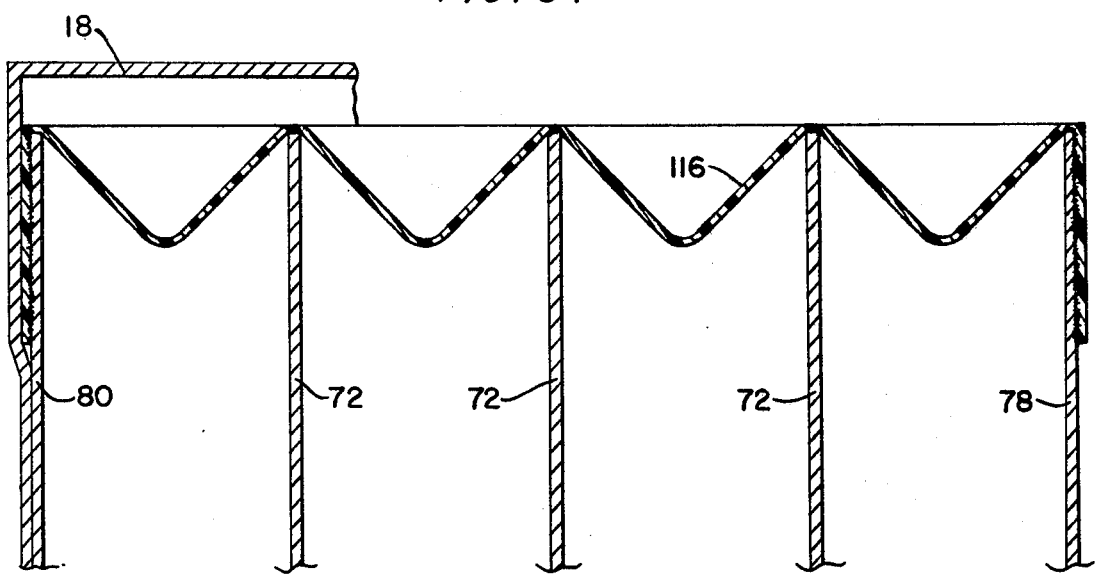
Figure 9:
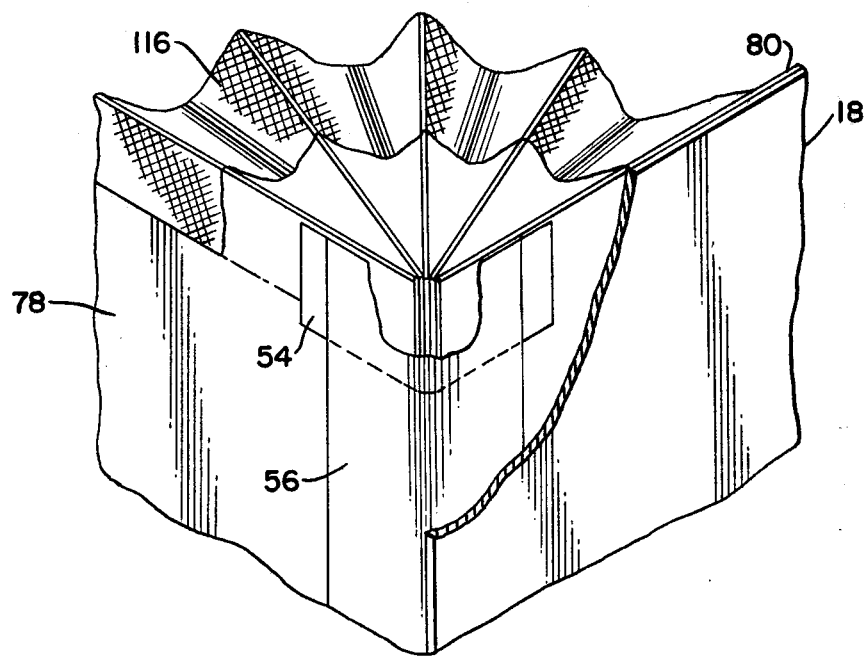
Figure 10:
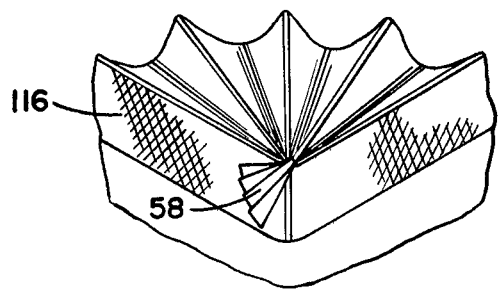
Figure 23:
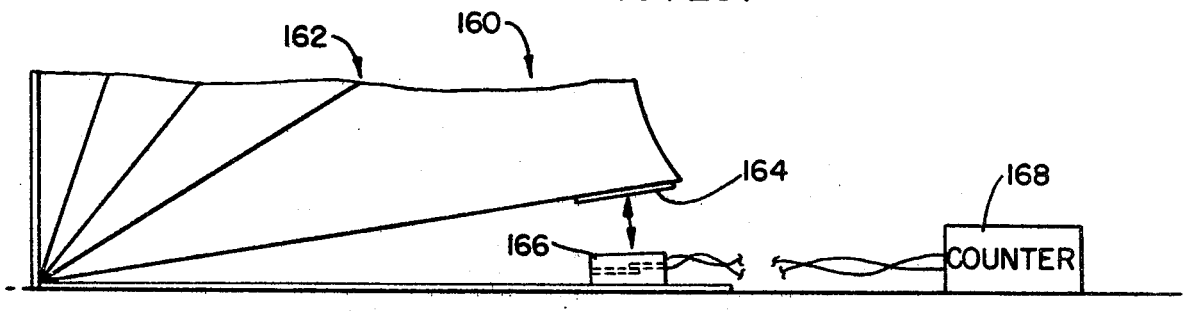
Figure 24:
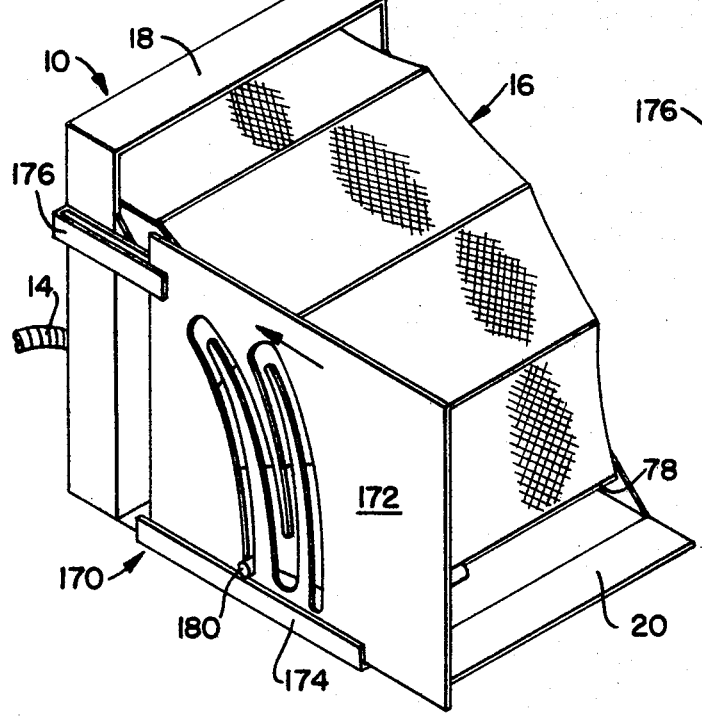
Figure 25:
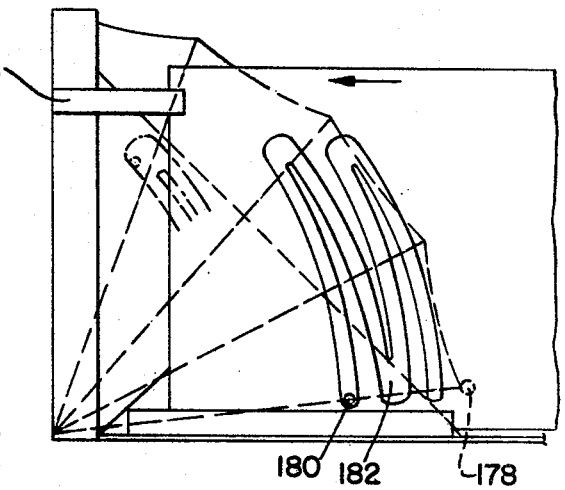

FIGS. 4 and 5 are partial cross-sectional views taken on lines 4—4 and 5—5 respectively of FIG. 1;

FIG. 6 is a view showing the manner in which the invention folds for storage;

FIG. 7 shows a folded and sealed package containing the invention;

FIG. 8 is a partial cross-sectional view taken on line 8—8 of FIG. 2;

FIG. 9 is a perspective view of the hinge portion of the preferred embodiment with some parts broken away;

FIG. 10 is view similar to FIG. 9 showing another detail of the bellows construction;

FIG. 11 is a perspective view of optional feature used in conjunction with the mouthpiece;

FIG. 12 is a view like FIG. 11 showing an optional mouthpiece and another optional feature;

FIG. 13 is a perspective view like FIG. 1 of a second embodiment of the invention;

FIG. 14 is a partial cross-sectional view taken on line 14—14 of FIG. 13;

FIG. 15 is a perspective view of a third embodiment of the invention;

FIG. 16 is a perspective view showing the manner of folding the third embodiment;

FIG. 17 is a perspective view of a fourth embodiment;

FIG. 18 is a view similar to FIG. 17 showing part of a fifth embodiment;

FIGS. 19 to 21 are schematic diagrams useful to help explain various features of the invention;

FIG. 22 is a schematic showing of the invention arranged for use as a spirometer;

FIG. 23 illustrates the optional feature of a counter which could be added to most of the forms of the invention;

FIG. 24 is a perspective view like FIG. 1 illustrating a sixth form which includes a recording arrangement;

FIG. 25 is a side elevational view of the form of FIG. 24; and

Figure 26:
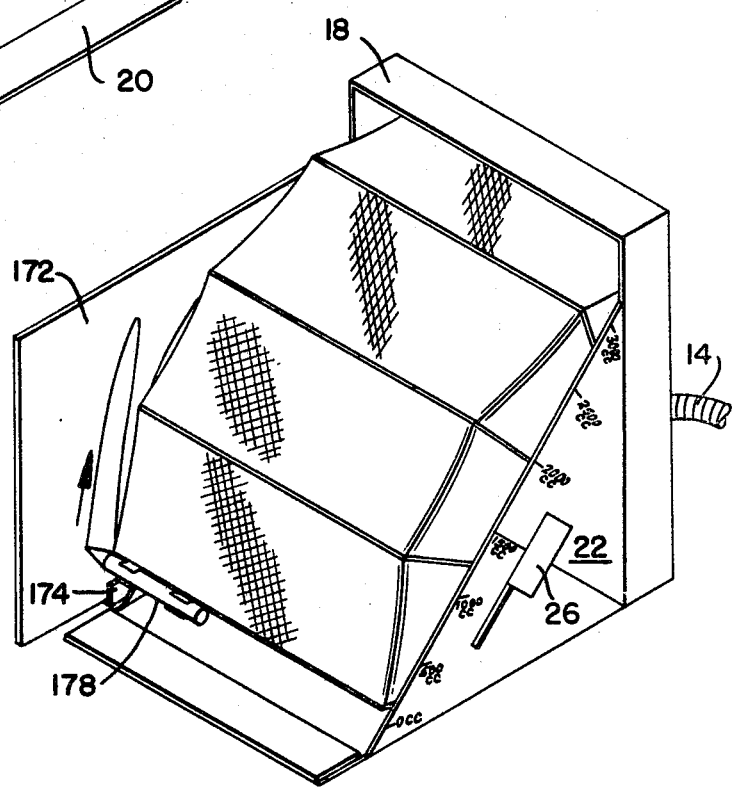

FIG. 26 is a perspective view of the opposite side of the form of FIG. 24.

Referring now in detail to the drawings, FIGS. 1 through 10 show the preferred form of the invention. In FIG. 7, the invention is shown folded and housed in an envelope 12. The invention 10 itself is shown removed from the envelope in FIG. 6, and is shown in assembled operative condition in FIGS. 1 and 2. In its folded condition, in the successful constructed embodiment of the invention illustrated, the box measures approximately 7¾ inches square by 1⅝ of an inch thick. As shown in FIG. 6, this includes the hose 14 which is coiled and nested into the box when it is folded closed.

Referring now to FIGS. 1, 3, and 6, the invention respiratory exerciser 10 comprises a bellows 16 secured to the tray portion 18 of a box-like structure which also comprises a lid 20 hinged at one edge to the tray portion 18 and joined thereto by a pair of triangular gussets 22. The details of these bellows 16 are shown in FIGS. 8, 9 and 10, and are described in greater detail below. As shown in FIG. 6, the bellows 16 collapse down into the tray, the hose 14 is stored on top of the folded bellows, and the gussets 22 fold inwardly on top of the hose and bellows. The lid 20 is brought down onto the open base of the tray portion 18.

Means are provided to hold the structure firmly in the assembled condition shown in FIG. 1 for use. To this end, each gusset 22 has a slot 24 formed therein which runs parallel to the long side or hypotenuse see FIG. 5. Mounted in each slot 24 is a gusset assembly clip 26. Lid 20 serves as the base when in use as in FIG. 1, the structure in effect being turned upside down from the opening position of FIG. 6 to the use position of FIG. 1. The length of each slot 24 is such with respect to the length of the clips 26 that the clips may be moved onto one half of the folded gusset for folding, and then are slid to the other part of the slot 24 for assembly. An indicator clip 28 is also provided for sliding motion on the hypotenuse of the gusset 22. Clip 28 is shown in FIGS. 1 and 5, and its function will be explained below.

The box comprising tray portion 18, the lid 20 and the gussets 22 is a more or less conventional cardboard box and is manufactured using conventional techniques in that art. Die cutting of paper board and the general business of folding boxes is highly developed. Durable products are produced at relatively low cost, and the present invention uses that fact to great advantage. The bellows 16 is in effect a separately manufactured subassembly which is glued into the box, as will be described in greater detail below.

Means are provided to permit ready mounting and dismounting of hose 14. Two different forms of this structure are shown in FIGS. 2 and 3. Referring to FIG. 2, a pad or block 30 of a particular type of foamed plastic material is secured as by gluing to the inside of the bottom wall of the tray portion 18 in alignment with an opening 32 in that wall. The hole in the foam 30 is slightly smaller than the opening 32 in the tray, and is also slightly smaller than a ridge 34 on hose 14.

As is fairly obvious, the hose is mounted by simply forcing the ridge 34 on the hose through the slightly smaller opening in the foam pad 30. In this manner a secure and air tight seal is formed, which seal is broken by simply tugging on the hose to pull the ridge 34 out beyond the pad 30. Pad 30 is formed of a so-called closed cell or closed pore type of plastic so that no particles will be abraded off by the repeated insertion and removal of hose 14. Such foams are well known in the art, and one is sold under the trademark "Ethafoam". The closed cell foam is important so that powders or flakes not be generated by the motion of the hose through the foam pad, which particles or flakes could possibly be inhaled by a patient.

Another important advantage of the invention is that the hose 14 is standard medical tubing. It comes in continuous rolls with a short repeat cycle of a corrugated section and a shoulder and ridge section 34, which permits mounting of mouthpieces (as shown in FIG. 4, for example), as well as providing the ridge 34 for mounting to the back of the exerciser itself. This hose is the subject of U.S. Pat. No. 3,794,080 to Houston et al, and reference can be had to that patent for more detail for such hoses, if deemed necessary to complete this teaching.

FIG. 3 shows a variation of the foam block 30, namely a thin sheet of rubber 36. The advantage of rubber is that all likelihood of flaking is eliminated. The foam is preferred because it forms a tighter seal and grips the hose tighter due to its greater thickness. Another advantage of the foam is that it is less expensive, lighter in weight, and easer to use than rubber sheeting. However, the second embodiment of the rubber sheet 36 can be used and in fact is used in other medical environments.

Referring now to FIG. 4 there is shown one form of mouthpiece 38 and its attachment to hose 14. A second form is shown in FIG. 12 described below. Mouthpiece 38 is of tubular configuration slightly flared outwardly towards the user. It comprises a molded bead 40 which fits within the ridge portion 34 of the hose 14. The hose is cut off of the roll so that some of it can be stretched over the mouthpiece, as shown.

An important feature is a screen 42 at the end of the mouthpiece itself. Screen 42 in the successfully constructed embodiment is a small piece of fine mesh polyethylene screening which is welded or heat sealed to the end of the mouthpiece, as shown most clearly in FIGS. 4 and 12. The portion 44 to the right of screen 42 in FIG. 4 is the first corrugation of the hose.

The provision of a screen 42 at the mouthpiece rather than at any other location provides important advantages. Some prior art devices include no user screen at all. This is deemed highly undesirable and dangerous. For example, bits of material left over from manufacturing, dirt, dust and even an insect, could find their way into the device and, absent the screen, such foreign material could be inhaled by a user, with possible disasterous effects. Other prior art devices include screens elsewhere, for example, between the hose and the device. Such locations are less desirable since the hose is still susceptable to intrusion by foreign materials and later inhalation by the user. By providing the screen directly at the mouthpiece as in the invention, the possibility of inhalation of foreign material is reduced to virtually zero. Any user is likely to look at the mouthpiece before putting it in his mouth. Further, as shown in FIG. 12, the provision of the screen directly at the mouthpiece permits removal of the mouthpiece from the hose, by simply "unpopping" the bead 40 from the inside of the ridge 34 on the hose. The mouthpiece also permits addition of other items, as described below, between the mouthpiece and the device, while at the same time keeping the advantage of the final screen just before the user to filter out foreign material.

Referring now to FIGS. 8 to 10, one method of fabrication of a bellows 16 is shown in detail. This is the first form of the invention which was developed by the present inventors. It is operative, but it has been superseded in the commercially marketed exerciser by another bellows covered by a separate patent application filed by one of the present inventors, Norman R. McCombs, et. al. The bellows of this and of the companion patent application are interchangeable, and either could be used depending upon the particular constraints of a particular environment.

Bellows 16 is basically a taped and glued assembly of cut flat pieces. The sheet material is folded in a particular manner so as to provide an air tight bellows while at the same time being resistant to tearing or deterioration from repeated use.

Referring now to FIG. 8, there is shown the intermediate, bottom and top vanes, 72, 78 and 80, respectively, all with respect to the plastic sheeting material 116 covering the vanes to form the bellows. The angularity of the vanes has been removed and FIG. 8 in general has been simplified to best show the construction. The manner of mounting the bellows in the tray portion of box 18 is also shown. FIGS. 9 and 10 show how the structure is built up. The edges of the sheeting 116 are first wrapped over and then glued to the edges of the outer vanes 78 and 80. Tape 54 for re-enforcing is provided top and bottom, and the hinge-like action is completed by another tape 56 which overlies the tapes 54. Tapes 54 in turn overlie the edges of the sheeting material. FIG. 10 shows this intermediate step, namely the manner in which the excess material of the sheeting material 116 is furled as at 58 and folded over to one side, before the tape 54 shown in FIG. 9 is applied.

This combination of the furled edge 58 of the sheeting material 116, reinforced first by end tapes 54 and then by the longitudinal tape 56, have been found to form a strong and durable bellows hinge.

FIGS. 11 and 12 show some other facets of the versatility of the invention in regard to mouthpieces. FIG. 11 shows a mister 46 between mouthpiece 38 and hose 14. Such a device might be needed where the patient requires the addition of moisture to the air which he is breathing. Such a device is shown only generally at 46 in FIG. 11, it could also include dispensing devices for medicine, and the like.

Another advantage of the invention, particularly with respect to its indicating scales and its recording aspects described herein, is that the bellows motion is directly proportional to the amount of medication inhaled by the patient, which is of course very important information in treating the patient.

FIG. 12 shows another mouthpiece 38A which has an open or flared portion to go into the user's mouth. Such a mouthpiece is frequently used in tandem with a breather or carborator device 48. Both devices 46 and 48 will include internal portions to cooperate with the mouthpiece and with the hose, all in a more or less conventional manner in this art. The mouthpiece arrangement of FIG. 12 is provided where the user might be more comfortable with a flared rather than a round mouthpiece, or where a smaller flow of air is needed. The top opening 50 is manually closed off by the user with one finger so that air will be drawn only through the device, and then released to permit a larger flow of air than would be provided through the relatively smaller flared end 52 of the mouthpiece 38A so that the bellows will return quickly and easily between efforts by the patient.

The mouthpiece 38 of FIG. 8 is slightly preferred because of its relatively lower cost and greater ease of manufacture. This mouthpiece 38 is a simple cut off piece of standard medical tubing with the screen 42 welded or sealed to the inside end thereof, and thus it is preferred, from the manufacturer's point of view, to the flared mouthpiece 52 of FIG. 9, or to other mouthpieces which could be used. The invention of course includes and can be used with any such mouthpiece.

Means are provided to permit the vanes in the bellows to clear the intrusion of the end of the hose 14 including the ridge 34 and the foam block 30. To this end, the intermediate vanes 72 of bellows 16 are formed with openings 74 which will clear the block 30 and hose end 34 in the raised and the folded condition of the bellows.

The invention also provides, in conjunction with the indicator clip 28, means to indicate the volume of air inspired by a user. To this end, a scale 76, typically in cubic centimeters (cc's) as is common in the medical area, is printed on the gussets 22 on both sides thereof to facilitate their observation by the user. The moving bottom vane 78 of the bellows 16 automatically is the indicator in cooperation with scale 76 to indicate volume of air inspired out of the bellows. The remaining vane 80 of bellows 16 is secured as by gluing to the inside of the tray portion 18 of the box.

A second embodiment 82 of the invention is shown in FIGS. 13 and 14. This form of the invention is characterized by a fixed frame of a general "L" shape (viewed edgewise) with the bellows secured thereto, as opposed to the folding box form. This version comprises a vertical wall 84 having a tubular extension 86 to which hose 14 is fitted, and a horizontal wall 88. The bottom vane 94 is cut out of the bottom wall 88 to leave the opening 90 shown in the drawings. In this manner, a single fold or bend in a single sheet to create the walls 84 and 88 at the same time creates the hinge for the bottom vane 94.

The two walls 84 and 88 are interconnected by a strap 92 which rigidifies the structure. Strap 92 could be foldable like the hinges on a briefcase so that this version could also fold.

This form of FIGS. 13 and 14 also comprises indicator means so the user will know how well he is doing in increasing his lung capacity. To this end, the bottom vane 94 carries an offset arcuate scale which operates with a pointer 98 to indicate the volume inspired, in an obvious manner. This second embodiment 82 may have the sheet material 100 forming the bellows secured directly to the vertical wall 84 (see FIG. 14), as well as to the ends and sides of the vanes as described above.

FIGS. 15 and 16 show another variation housed in a box, but which folds in a different manner. This third embodiment 102 comprises a lid 104, a pair of rigid triangular gussets 106, and a tray portion 108 which houses the bellows 110. Velcro fasteners 112 secure the lid 104 to the gussets 106 in assembled condition, and another pair of similar fasteners 114 secures the lid down to the tray in the folded condition. The fasteners 112 and 114 are exemplary only; mating slots and tabs, snaps, and the like could be used. Scales 76 as in the first embodiment are provided on both sides of gussets 106.

This third embodiment illustrates a variation of the bellows, in addition to the form of the box. This bellows 116 comprises a bottom vane 118, a middle vane 120, and a vane at the top which is fixed to the inside of the tray portion 108. A strap 124 internally of the bellows is provided to assist in holding the positions of the vanes. As will be explained in greater detail below in conjunction with FIGS. 19, 20 and 21 this form of bellows is deemed less desirable than the multi-vane type, but it may be useable in other applications and environments.

This third embodiment, while viable and operative, is not the preferred form of the invention because it is deemed that the rigid fold out gussets are slightly more complex to assemble than the folding gussets of the FIG. 1 form. However, in other environments and in other situations, it could be the first choice.

FIGS. 17 and 18 show fourth and fifth embodiments 126 and 128 respectively which are close in concept to the FIG. 14 embodiment. Therefore, parts the same as or similar to parts described above will be indicated by the same reference numeral followed by "A".

The two embodiments of FIGS. 17 and 18 are similar to each other and different from the FIG. 13 embodiment in that separate means are provided to hold a separate and replaceable bellows. Thus, a semi-permanent two-part structure is provided in the case of embodiments 126 and 128, a relatively permanent holder type structure, and an easily replaceable bellows.

Referring to FIG. 17, the walls 84A and 88A comprise a separate holder, together with the strap 92A and the nozzle 86A. A separate bellows assembly 130 is provided, having a horizontal vane 132 formed with a cutout 134 for receiving the nozzle 86A. A plurality of vanes 136 and a cover membrane 138 connect together to a moving bottom vane 140. This bottom vane 140 carries the scale 96A which cooperates with the pointer 98A carried on fixed vertical wall 84A.

Thus, the embodiments 126 uses whatever advantages reside in the prior art permanent devices, together with the relatively simple concepts of the present invention bellows 130. The hospital or other user may keep a supply of the holders comprising the walls 84A and 88A on hand and can interchange bellows as necessary, and of course can provide hoses for cooperation with the nozzles 86A.

The second embodiment 128 of FIG. 18 comprises a relatively small holder bracket 142 which comprises a bifurcated vertical wall 144 which receives a nozzle or tubular extension 146 on the vertical vane 148 of this bellows assembly 150.

FIGS. 19 and 20 are highly schematic and illustrate some principles and certain facets of the bellows used in all embodiments of the invention. The preferred form of the bellows is shown in FIG. 19, and a less preferred form is shown in FIG. 20. It has been found that a plurality of vanes which have equal length along the radial lines of the bellows perform better than a bellows having a relatively smaller number of vanes and better than vanes which do not have the same length radially. In FIGS. 19 and 20, dotted lines indicate the sweep line defined by the end of a vane, the dot-dash line represents the hypotenuse of the box or holder containing the bellows.

Referring to FIG. 19 it can be seen that the preferred form makes the action of the bellows much more linear. That is, the plurality of wedge shapes defined by the vanes close in a more or less equal manner as the bellows goes from the open position of FIG. 19a to the more fully closed position of FIG. 19c. This is deemed to occur because the relatively large number (four in FIG. 19) of pie shaped wedges or segments which are formed. Looking at FIG. 20, it can be seen that the right hand wedge shape closes up much more rapidly than does the left hand one. This is highly undesirable in use, since the user will experience a rapid change at the end of his breath rather than a smooth action all the way through. However, one cannot increase the number of vanes indefinitely since there will come a point where the weight and resistance to closing added by the vanes themselves will have a detrimental effect.

FIG. 20 also illustrates the shorter vane length, one defined by the hypotenuse of the box. The only advantage of this configuration is that it is simpler to manufacture the vanes of FIG. 20 than the vanes of FIG. 19 using paper box die cutting techniques. However, this relatively minor advantage is more than overcome by the improved performance by the preferred form. FIG. 20a shows what the vanes would look like were they cut to conform to the hypotenuse line 152 of that box.

As to the linear nature of the closing action, as the bellows comes near the end of its closing motion, it would close up at an increased speed, and the volume would become very small at the end because of the vanes coming rapidly up against the end of the bellows. This is the facet which provides the undesirable effect in FIG. 20 which is not present in FIG. 19.

FIGS. 19 and 20 also suggest another facet of the flexibility of the invention, i.e., the bellows can be made to accomodate various sizes and many different applications by simply varying the length of the vanes. Further, in other areas, perhaps in non-medical areas, the non-linear response may not be a disadvantage. Thus, by making the vanes shorter, the same size box can accomodate a smaller volume bellows than could be accomodated in the same box by making the vanes radial as indicated in FIG. 19. Thus, in those applications where the non-linear closing effect does not matter, the same size box or housing or bracket or the like can be made to accomodate bellows having substantially different volumes by using one or the other of the hypotenuse lines or radial line bellows structures as illustrated in these two figures.

Along this same line of thinking, yet another aspect, shown in FIG. 21, is one wherein a single sheet of cardboard or the like is folded in half, and the two sides are joined together by a membrane with no intermediate vanes. This variation could be housed in a box as in FIG. 1, could be a hybrid device such as in FIG. 13, could be a semi-permanent device such as FIG. 17 or 18, or could be completely separate and not housed in a box or holder at all. The invention thus includes forms having no box, holder or the like, i.e., embodiments which comprise a bellows only.

Thus, it can be seen that the invention resides primarily in the bellows. It can be housed in and be a integral part of a carrying and storage box, can be a semi-permanent device as in FIGS. 17 and 18, or can be completely separate, that is a bellows alone, as in FIG. 21.

The bellows is perhaps the single most important part of the invention. It is characterized by being of relatively simple construction, often comprising little more than folded and/or cut pieces of carboard over which is mounted inexpensive plastic sheeting material to form the bellows. One or more holes are provided as necessary for access to the inside of the bellows. This is to be compared with the prior art bellows which are often involved devices comprising complex parts of molded rubber or the like, internal springs, relatively great weight, and the like, all of which disadvantages are overcome by the present invention bellows. In place of these materials and highly complex molding techniques and the like, the invention bellows, most basically, simply comprises cardboard over which inexpensive air impervious sheet material is stretched and glued.

As shown in FIGS. 1 and 17, the cutouts 74 and 134 in the vanes cooperate with the position of the hole or nozzle of hose 17, and these positions are the result of a balance of practicality. The hole or nozzle must be high enough so that it is readily usable for mounting and dismounting of the hose. It also must be low enough so that it does not tip over the device in use. Further, it needs to be out of the way of the bellows during its closing motion. The cutouts could be made relatively larger up to the limit of providing a reasonable amount of rigidity to the vanes in use. The intrusion of the hose and the block 30, or the back of the nozzle, must be balanced against the thickness of the vanes to permit full closing of the bellows. All of this is easily handled by those skilled in these arts.

In regard to the membrane used for the bellows, such as film 138 in FIG. 17, it is desired that it be of a type and quality that will not stick to itself during opening and closing of the bellows. Further, it is preferred that it be relatively inexpensive, and yet durable to withstand the manufacturing process and later use. It has been found that embossed polyethylene, preferably translucent for esthetic effect only, is highly successful. The commercial form of the invention uses embossed blue polyethylene which is translucent and is 0.0015 inches in thickness. The embossing aids in the folding and unfolding of the film in the opening and closing motion of the bellows. Opaque and other films could, of course, also be used.

Referring now to FIG. 22, there is shown a sixth embodiment 154 of the invention. This form illustrates that the invention can be used as a conventional spirometer. A spirometer works with the user's ability to exhale rather than the user's ability to inhale, as in the forms of the invention described above. To this end, embodiment 154 includes blocks or other means 156 to raise the bellows above the supports to allow clearance of elbow 158 connected to the hose 14. An exhalation by the user via hose 14 will cause the bellows to open and expand against gravity as indicated by the arrows. Termination of the breath will allow the bellows to collapse under the force of gravity alone. Weights or other means could be provided on the uppermost vane to assist in closing or to control the action of the embodiment 154.

FIG. 23 shows a seventh embodiment 160 which comprises means to count the cycles of operation of bellows 162. This bellows 162 represents the moving part of any embodiment of the invention. The counter comprises a small piece of magnetic material 164 which operates a reed or similar switch 166 which in turn drives a counter device 168, all as is evident from the drawing.

FIGS. 24, 25 and 26 show an add-on feature, shown mounted on the first embodiment 10, to record the motion of the bellows to produce a permanent record of the user's progress. To this end, the recording device accessory 170 comprises a card 172 which is mounted on a removable sliding track 174 and a guide 176 both made of lightweight plastic and designed to removably snap onto the lid 20 and the tray 18, respectively. Bottom vane 78 carries a pencil or other card marking means 178 and a pin 180 which fits into a serpentine slot 182. Both the marker 178 and pin 180 are built so as to be easily mounted on the device 10 so as to selectively convert it to a record marker.

The serpentine slot 182 is arranged so as to have four separate sections. The configuration of each section designed with respect to the motion of the bellows such that the pin 180 will reciprocate back and forth in only one slot section at a time. Pin 180 is put by the user into another of the four slots when it is desired to make additional traces. In FIG. 26, two of such trace families are illustrated. If the size and configuration of the parts can be made and the durability of the materials are such, more than four slots could be provided in card 172.

It will of course be understood that other equivalent means to produce a permanent record such as ball point pens, felt tip pens, ratchet gears, stationary cards, or whatever could also be provided to produce a permanent record of the motion of the bellows. Further, card 172 can advance by itself if the device is placed on an incline. In that case, the pen pushes the card forward.

While the invention has been described in detail above, it is to be understood that this detailed description is by way of example only, and the protection granted is to be limited only within the spirit of the invention and the scope of the following claims.

We claim:

1. An air handling device comprising a bellows which expands and collapses in book-like fashion, said bellows comprising a pair of outer vanes and at least one other vane between said outer vanes, hinge means joining one corresponding portion of all of said vanes together to permit said book-like expanding and collapsing of said bellows, air impervious sheet material fixed to said corresponding portions of said pair of outer vanes to form a substantially air-tight space within the bellows defined by said pair of outer vanes and said sheet material, air flow means to provide access for air into and out of said bellows adapting said device to function as an incentive breathing exerciser; all of said vanes, said sheet material, said hinge means, and said access means being so selected that said bellows is sufficiently inexpensive that it may be disposed of after a single user is done using it, wherein one of said outer vanes is a moving vane and moves with respect to the other of said outer vanes during use of said device, said other of said outer vanes being a non-moving vane, and mounting means for mounting said non-moving vane substantially vertically during use of said exerciser with said hinge means at the lower end of said non-moving vane, whereby the force of gravity tends to pull said moving vane and re-expand said bellows after each user's inspirational breath collapses said bellows, and whereby each user's inspirational breath collapses said bellows by drawing said moving vane against the force of gravity towards said non-moving vane.

2. The combination of claim 1, wherein said mounting means comprises box means to house said bellows, and means to fix said non-moving vane into said box means.

3. The combination of claim 2, wherein said air handling device further comprises means to make a permanent record of the motion of said bellows as a user exercises his respiratory ability, said record means comprising recording card means, means to mount said recording card means to said box means, marking means carried by said moving vane and positioned to mark said recording card means as said moving vane moves during use.

4. The combination of claim 3, wherein slot means are formed in said recording card means, guide pin means on said moving vane cooperable with said slot means, said guide pin means being located on said moving vane in spaced relation to said marking means on said moving vane, said slot means being of serpentine configuration and one slot run only of said serpentine slot means at a time being cooperable with said guide pin means, whereby a series of trace families equal to the number of turns in said serpentine slot means can be created by said marking means on one of said recording means.

5. The combination of claim 3, wherein removable clip means are provided to removably mount said recording card means on said box means.

6. The combination of claim 1, wherein all of said vanes being formed of thin flat material, whereby said bellows when collapsed occupies a volume approximately equal to the volume of all of said vanes were all of said vanes in a stack.

7. The combination of claim 6, wherein all of said vanes consist of cardboard.

8. The combination of claim 6, wherein said sheet material consisting of embossed polyethylene, said hinge means comprising tape, and glue joining said polyethylene to all of said vanes.

9. The combination of claim 6, wherein all of said vanes being of rectilinear shape, said air flow means comprising a length of respiratory hose and a mouthpiece, said mounting means comprising box means and means to fix said bellows in said box means, and said box means being of compact size but large enough to enclose and store said hose, said mouthpiece and said bellows when collapsed; whereby said device may be stored in a relatively small space.

10. The combination of claim 9, wherein said sheet material consisting of embossed polyethylene, said hinge means comprising tape, glue joining said sheet material to all of said said vanes, and said bellows being glued into said box means.

11. The combination of claim 1, wherein said sheet material consists of embossed polyethylene.

12. The combination of claim 1, wherein said mounting means comprises box means and means to fix said bellows in said box means, said box means comprising a tray portion and a lid portion hinged to said tray portion adjacent said hinge means, folding gusset means to hold said lid portion in the substantially fully open position, whereby said lid portion is at a substantially right angle with respect to said tray portion, and said non-moving vane of said bellows being glued into said tray portion.

13. The combination of claim 12, wherein said folding gusset means comprises at least one triangular folding gusset joined at one side to said tray portion and at its other side to said lid portion, said gusset being adapted to fold substantially in half as said lid portion is closed onto said tray portion on a line substantially at right angles to the hypotenuse of said triangular gusset, and said gusset comprising means to hold said gusset unfolded and relatively rigid in the substantially fully open position of said lid portion.

14. The combination of claim 13, wherein said last-mentioned means comprises a slot formed in said gusset, a clip slidingly mounted in said slot, and the length of said clip and the length of said gusset slot being such that said clip can be located in a first position away from said fold line in said gusset to permit said gusset to fold and said lid portion to close and in a second position on said fold line so that said gusset rigidly holds said lid portion with respect to said tray portion in the substantially fully open position of said lid portion.

15. The combination of claim 14, wherein said gusset means comprises a pair of said gussets both formed with slots each carrying one said clip.

16. The combination of claim 15, wherein each of said folding gussets has the general configuration of a 45 degree right triangle, in the substantially fully open position of said lid portion, and the hypotenuse edge of said gussets comprising scale means for indicating in cooperation with said moving vane the volume of air inspired by a user during use.

17. The combination of claim 16, wherein said scale means are provided on both faces of both of said gussets, whereby a user can readily see at least one of said scale means from virtually any position with respect to said device.

18. The combination of claim 17, wherein moveable target means are mounted on said gussets for cooperation with said scale means to aid the user in increasing his lung capacity.

19. The combination of claim 12, wherein all of said vanes and said box means being of generally rectangular configuration and consisting substantially entirely of cardboard.

20. The combination of claim 12, wherein said folding gusset means comprises at least one gusset comprising a triangular relatively rigid portion of said box hinged at one side thereof to said tray portion, and means at the other side of said triangular gusset to permit its removable joining to said lid portion in the substantially fully open position of said lid portion.

21. The combination of claim 20, wherein said gusset means comprises a pair of said triangular gussets joined to opposite edges of said tray portion, and said gussets being such that they will overlie each other and the folded and collapsed bellows within said tray portion.

22. The combination of claim 21, wherein each of said gussets has the general configuration of a 45 degree right triangle in the substantially fully open position of said lid portion, and the hypotenuse edge of said gussets comprising scale means for indicating in cooperation with said moving vane the volume of air inspired by a user during use.

23. The combination of claim 21, wherein scale means are provided on both faces of both of said gussets, whereby a user can readily see at least one of said scale means from virtually any position with respect to said device.

24. The combination of claim 23, wherein moveable target means are mounted on said gussets for cooperation with said scale means to aid the user to increase his lung capacity.

25. The combinaton of claim 20, wherein said gusset is integrally hinged to an edge of said tray portion.

26. The combination of claim 20, wherein all of said vanes and said box means being of generally rectangular configuration and consisting substantially entirely of cardboard.

27. The combination of claim 1, wherein said sheet material being gathered together with joining means at said hinge means, said sheet material being joined to the portions of all of said vanes remote from said hinge means such that said sheet material defines the positions of all of said vanes and the configuration of said bellows at maximum expansion.

28. The combination of claim 1, wherein a plurality of said other vanes are provided between said outer vanes.

29. The combination of claim 28, wherein said air flow means comprises an opening in said non-moving vane and communicating with the inside of said bellows, and said other vanes having clearance openings to clear said opening when said bellows is collapsed.

30. The combination of claim 28, wherein all of said vanes are of the same radial length out from said hinge means.

31. The combination of claim 28, wherein at least some of said other vanes are of shorter radial length out from said hinge means than said outer vanes, and said outer vanes being substantially equal to each other in said radial length dimension.

32. The combination of claim 28, wherein three vanes are provided between said pair of outer vanes.

33. The combination of claim 28, wherein said sheet material being gathered together with joining means at said hinge means, said sheet material being joined to the portions of all of said vanes remote from said hinge means such that said sheet material defines the positions of all of said vanes and the configuration of said bellows at maximum expansion, and said sheet material being joined to all of said vanes such that the spaces between each two of all of said vanes is substantially equal.

34. The combination of claim 1, wherein said air handling device being useful in medical applications for human respiration, said air flow means comprising an opening formed at a predetermined location in said non-moving vane, said air flow means further comprising a length of medical respiration tubing having a first end and a second end, means to removably join an end of said tubing to said device at said opening, said last-mentioned means comprising a cylindrical section of said tubing at said first end thereof and an enlarged bead at the first end of said cylindrical section, said opening having an axis and being provided with sealing means having an opening, said opening through said sealing means being slightly larger than said cylindrical section of said tubing and slightly smaller than said enlarged bead, whereby said bead may be moved past said opening by virtue of a yielding quality of said sealing means, whereby a substantially air tight seal is formed by said sealing means around said cylindrical section of said tubing.

35. The combination of claim 34, wherein said sealing means comprises a block of closed cell plastic foam.

36. The combination of claim 34, wherein said sealing means comprises a sheet of rubber.

37. The combination of claim 34, wherein said sealing means being secured to said non-moving vane on the inside of said bellows in axial alignment with said opening.

38. The combination of claim 34, wherein mouthpiece means is provided at the second end of said tubing.

39. The combination of claim 1, wherein said mounting means comprises a reusable holder for said bellows.

40. The combination of claim 38, wherein said holder comprises a pair of walls at substantially right angles to each other with said bellows being removably mounted in said holder, and scale means mounted on said moving vane and an indicator means mounted on said non-moving vane, whereby said scale means is driven by said moving vane past said indicator means for indicating the air inspired by a user.

41. The combination of claim 40, wherein said non-moving vane of said bellows being formed with a portion of said air flow means cooperable with a portion of said air flow means in said holder.

42. The combination of claim 39, wherein said holder comprises a hose wall adapted to be horizontally disposed and a short bifurcated vertical wall, said air flow means comprising nozzle means extending from said non-moving vane of said bellows, and means to mount said nozzle means in said holder bifurcated wall to thereby mount said bellows in said holder.

43. The combination of claim 1, wherein said air flow means comprises a length of hose, means to removably connect said hose to said bellows at said non-moving vane, comprising an opening formed in said non-moving vane, and means to form a substantially air tight seal between said hose and said opening.

44. The combination of claim 43, wherein said means to form a seal comprises a block of closed cell plastic foam.

45. The combination of claim 43, wherein said means to form a seal comprises a thin sheet of rubber.

46. The combination of claim 1, wherein said air flow means comprises a length of hose, means to removably connect said hose to said bellows at said non-moving vane comprising a tubular extension extending outwardly form said non-moving vane, and means to form a substantially air tight seal between said hose and said extension.

47. The combination of claim 46, wherein said means to form a seal comprises a block of closed cell plastic foam.

48. The combination of claim 46, wherein said means to form a seal comprises a thin sheet of rubber.

49. An incentive breathing device comprising a folding bellows and air flow means adapting said bellows as an incentive breathing device, said bellows having means for operating said bellows with a book-like action and a folding box, said box comprising a lid and a tray hinged together, said bellows being mounted in said folding box for housing said bellows and air flow means of said device therein when in a folded closed position, a pair of triangular gussets interconnecting said lid and said tray said gussets being adapted to fold substantially in half as said lid is closed onto said tray on a line substantially at right angles to the hypotenuse of said triangular gussets, a slot formed in each of said gussets, a clip slidingly mounted in each of said slots, and the length of said clip and the length of said slot being such that said clip can be located in a first position away from said fold line of said gusset to permit said gusset to fold and said lid to close and in a second position on said fold line so that said gusset tigidly holds said lid at a substantially right angle with respect to said tray portion at a substantially right angle, whereby said lid is in a substantially fully open position.

50. The combination of claim 49, wherein each of said gussets has the general configuration of a 45 degree right triangle in the substantially fully open position of said lid, and the hypotenuse edge of said gussets comprising scale means for indicating in cooperation with said bellows the volume of air inspired by a user during use.

51. The combination of claim 50, wherein moveable target means are mounted on said gussets for cooperation with said scale means to aid the user in increasing his lung capacity.

52. The combination of claim 49, wherein all of said vanes and said box means being of generally rectangular configuration and consisting substantially entirely of cardboard.

* * * * *